United States Patent
Govari et al.

(10) Patent No.: US 11,096,741 B2
(45) Date of Patent: Aug. 24, 2021

(54) ABLATION POWER CONTROL BASED ON CONTACT FORCE

(71) Applicant: BIOSENSE WEBSTER (ISRAEL), LTD., Yokneam (IL)

(72) Inventors: Assaf Govari, Haifa (IL); Athanassios Papaioannou, Los Angeles, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 394 days.

(21) Appl. No.: 13/648,449

(22) Filed: Oct. 10, 2012

(65) Prior Publication Data

US 2014/0100563 A1 Apr. 10, 2014

(51) Int. Cl.
*A61B 18/00* (2006.01)
*A61B 18/14* (2006.01)
(Continued)

(52) U.S. Cl.
CPC .......... *A61B 18/1492* (2013.01); *A61B 34/10* (2016.02); *A61B 2018/00357* (2013.01); *A61B 2018/00577* (2013.01); *A61B 2018/00648* (2013.01); *A61B 2018/00696* (2013.01); *A61B 2018/00702* (2013.01); *A61B 2018/00738* (2013.01); *A61B 2018/00761* (2013.01);
(Continued)

(58) Field of Classification Search
CPC .......... A61B 2018/00577; A61B 2018/00702; A61B 2018/00761; A61B 18/12; A61B 18/14; A61B 18/1492
See application file for complete search history.

(56) References Cited

U.S. PATENT DOCUMENTS 6,226,542 B1 5/2001 Reisfeld
6,241,724 B1 6/2001 Fleischman
(Continued)

FOREIGN PATENT DOCUMENTS

EP 2 248 480 A1 11/2010
EP 2338428 A1 6/2011
(Continued)

OTHER PUBLICATIONS

European Search Report dated Jan. 27, 2014 from corresponding European Patent Application No. 13187214.5.
(Continued)

*Primary Examiner* — Jaymi E Della
(74) *Attorney, Agent, or Firm* — Lewis Roca Rothgerber Christie LLP

(57) ABSTRACT

Methods and systems are adapted for ablation of target tissue in a living subject by predicting a lesion size that would result from placing an ablation electrode into contact with the target tissue at a particular contact force while applying energy at a given power level for a particular time interval. The prediction involves modeling the lesion size as a non-linear function of the contact force, the power level and the time interval. The prediction may be iterated by varying the contact force, the power level or the time interval until a saturation point is found, beyond which the lesion size does not increase. After it is established that one of the iterations predicts a desired lesion size, ablation of the target tissue may be conducted using the contact force, the power level and the time interval of the one iteration.

12 Claims, 7 Drawing Sheets

(51) Int. Cl.
　　　*A61B 34/10*　　　(2016.01)
　　　*A61B 90/00*　　　(2016.01)
　　　*A61B 34/20*　　　(2016.01)

(52) U.S. Cl.
　　　CPC .............. *A61B 2018/00839* (2013.01); *A61B 2034/104* (2016.02); *A61B 2034/2051* (2016.02); *A61B 2090/065* (2016.02)

(56) References Cited

U.S. PATENT DOCUMENTS

| | | |
|---|---|---|
| 6,301,496 B1 | 10/2001 | Reisfeld |
| 6,695,808 B2 | 2/2004 | Tom |
| 6,814,733 B2 | 11/2004 | Schwartz |
| 6,892,091 B1 | 5/2005 | Ben Haim |
| 6,915,149 B2 | 7/2005 | Ben Haim |
| 6,997,924 B2 | 2/2006 | Schwartz |
| 7,156,816 B2 | 1/2007 | Schwartz |
| 7,306,593 B2 | 12/2007 | Keidar |
| 7,536,218 B2 | 5/2009 | Govari |
| 7,756,576 B2 | 7/2010 | Levin |
| 2004/0147920 A1* | 7/2004 | Keidar ..................... 606/34 |
| 2007/0100332 A1 | 5/2007 | Paul |
| 2008/0275465 A1 | 11/2008 | Paul |
| 2008/0288038 A1 | 11/2008 | Paul |
| 2010/0298826 A1 | 11/2010 | Leo |
| 2011/0118727 A1 | 5/2011 | Fish et al. |
| 2011/0152856 A1* | 6/2011 | Govari et al. ............... 606/34 |
| 2011/0251607 A1* | 10/2011 | Kruecker ........... A61B 18/1206 606/34 |

FOREIGN PATENT DOCUMENTS

| | | |
|---|---|---|
| EP | 2 499 982 A1 | 9/2012 |
| WO | WO 11034925 | 3/2011 |
| WO | WO 2012/092275 A1 | 7/2012 |
| WO | WO 2012092275 A1 * | 7/2012 |

OTHER PUBLICATIONS

Haines, D.E., Determinants of Lesion Size During Radiofrequency Catheter Ablation: The Role of Electrode-Tissue Contact Pressure and Duration of Energy Deliver, J Cardiovasc electrophysiol, 1991;2: 509-515.

Shimoike, E., Experimental Ablation Study Using a New Long Linear Probe in Isolated Porcine Hearts, Jpn Heart J 1999;40: 189-197.

European Exam Report dated Feb. 29, 2016 from corresponding European Patent Application No. 13187214.5.

* cited by examiner

ABLATION POWER CONTROL BASED ON CONTACT FORCE

BACKGROUND OF THE INVENTION

1. Field of the Invention

This invention relates to tissue ablation systems. More particularly, this invention relates to monitoring of contact between an invasive probe and tissue within the body.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 7,306,593, issued to Keidar et al., describes a method for ablating tissue in an organ by contacting a probe inside the body with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

The document *Determinants of Lesion Size During Radiofrequency Catheter Ablation: The Role of Electrode-Tissue Contact Pressure and Duration of Energy Delivery*, David E. Haines, J. Cardiovasc Electrophysiol, Vol. 2, pp. 509-515, December 1991 described the effects of varying electrode tissue contact pressure and duration of RF energy delivery on the size of the resultant lesion in an in vitro model of canine myocardium. A greater contact force significantly decreased the power required to maintain a constant electrode-tissue interface temperature, and the lesion size grew monoexponentially with time.

U.S. Patent Application Publication No. 2010/0298826 describes a force-time integral for real time estimation of lesion size in catheter-based ablation systems. The apparatus measures the force exerted by a contact ablation probe on a target tissue and integrates the force over an energization time of the ablation probe. The force-time integral can be calculated and utilized to provide an estimated lesion size (depth, volume and/or area) in real time. The force-time integral is said to possibly account for variations in the power delivered to the target tissue in real time to provide an improved estimation of the lesion size.

SUMMARY OF THE INVENTION

There is provided according to embodiments of the invention a method of ablation, which is carried out by inserting a probe into a body of a living subject, choosing a contact force between an ablation electrode of the probe and a target tissue, a power level and a time interval. The method is further carried out by predicting a lesion size that would result from placing the ablation electrode in a contacting relationship with the target tissue at the contact force while applying energy at the power level via the ablation electrode to the target tissue for ablation thereof for the time interval by modeling the lesion size as a non-linear function of the contact force, the power level and the time interval. The prediction is iterated after increasing one of the contact force, the power level and the time interval until a saturation point is found, wherein a further increase fails to result in an increased predicted lesion size. The method is further carried out by establishing that one of the iterations predicts a desired lesion size, urging the ablation electrode into the contacting relationship with the target tissue, and ablating the target tissue using the contact force, the power level and the time interval of the one iteration.

An additional aspect of the method includes graphically displaying the predictions during the iterations.

In one aspect of the method the iterations of making a prediction include varying the contact force and holding the power level and the time interval at constant levels.

In another aspect of the method the iterations of making a prediction include varying the power level and holding the contact force and the time interval at constant levels.

In yet another aspect of the method the iterations of making a prediction include varying the time interval and holding the contact force and the power level at constant levels.

There is further provided according to embodiments of the invention an ablation apparatus for carrying out the above-described methods.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
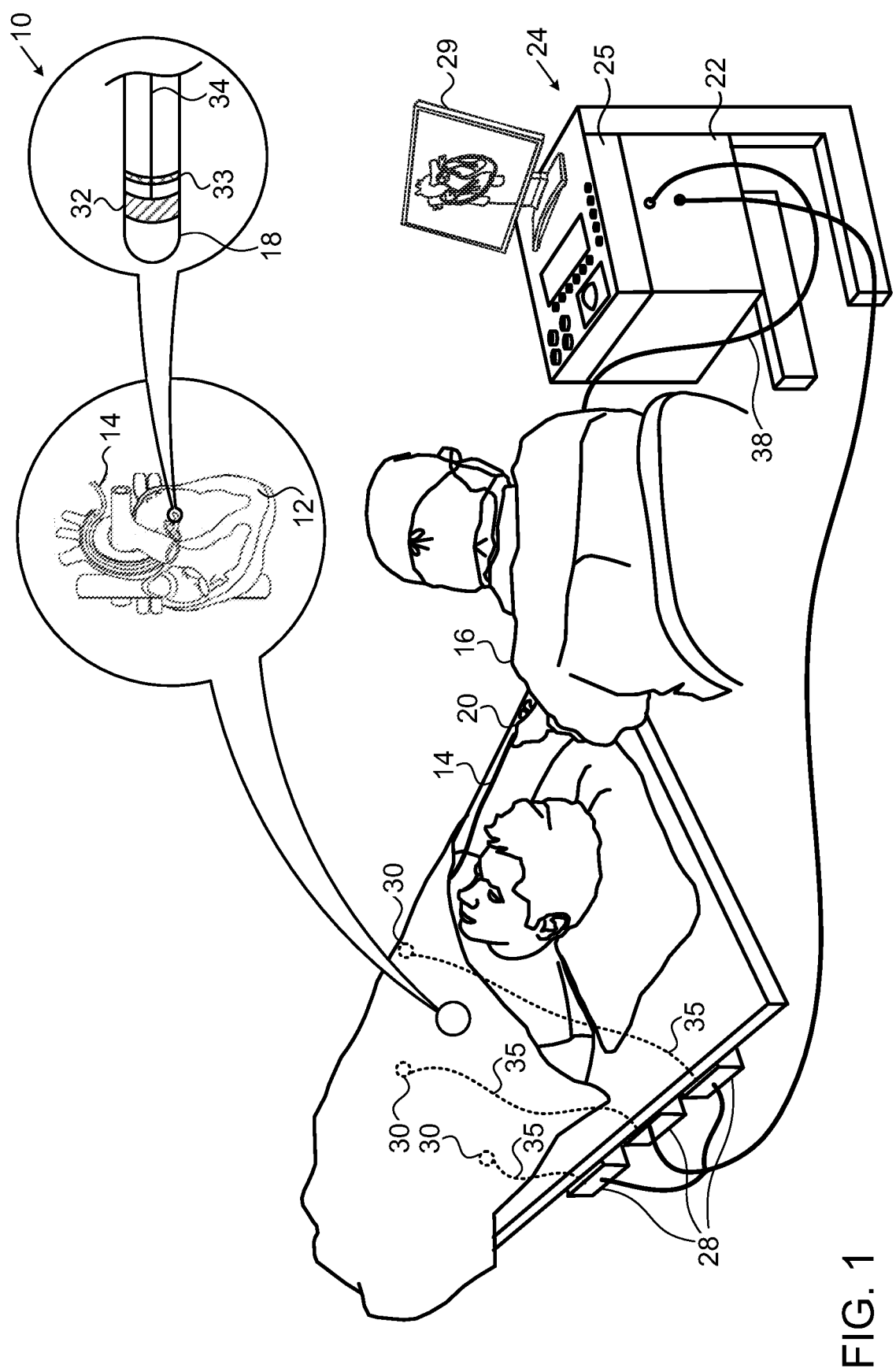
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
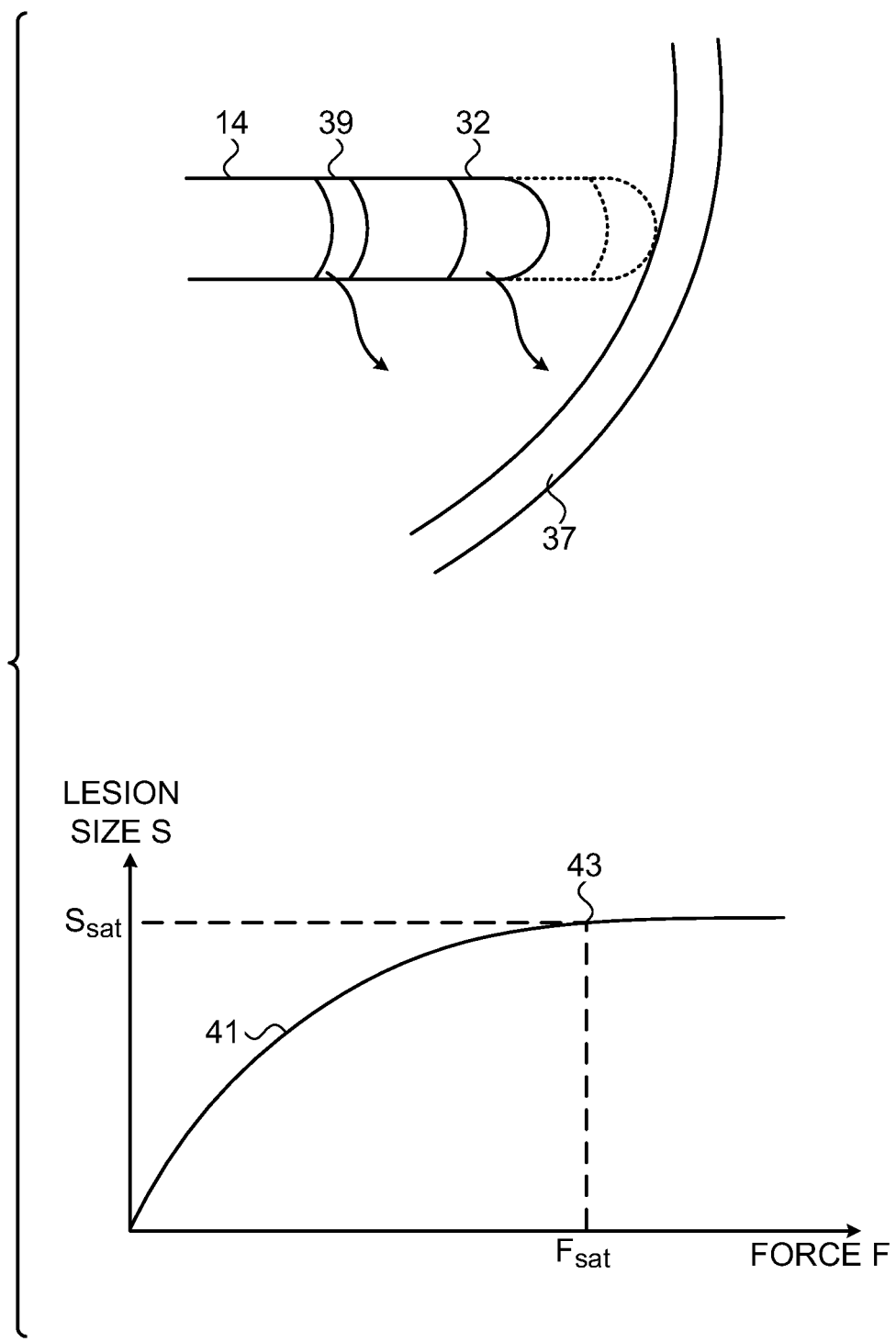
FIG. 2 is a composite drawing illustrating the relationship between contact force and lesion size, in accordance with an embodiment of the invention.

Reference is now made to FIG. 2, which is a composite drawing illustrating the relationship between contact force and lesion size caused by an ablation electrode of the catheter 14 when it has moved into contact with wall 37 of heart 12 (FIG. 1), in accordance with an embodiment of the invention. The inventor has discovered that there is a saturation effect when ablating tissue. Specifically, for a given ablation time interval T and a given ablation power P, the lesion size S for different forces F exerted by a catheter is given by curve 41, shown in the lower portion of FIG. 2. The curve 41 shows that as the force increases, the rate of change of lesion size (dS/dF), i.e., the slope of the curve, decreases. A point 43, ($F_{sat}$, $S_{sat}$), at which the slope is effectively zero, corresponds to a saturation point of the ablating system, since increasing the force to values greater than $F_{sat}$ does not change the lesion size $S_{sat}$.

Knowledge of the saturation effect may be used to determine the force needed to generate a desired lesion size (for a given power P and time interval T) in an ablation procedure. An expression relating lesion size S to force F may be written:

$$S = f(F, P, T) \quad (1).$$

Variations due to physical changes occurring during the cardiac cycle may be compensated by integration over time, as shown by equations (2) and (3):

$$ds = \frac{\partial f}{\partial F} dF + \frac{\partial f}{\partial P} dP + \frac{\partial f}{\partial T} dT; \quad (2)$$

and $$S = \sum_i S_i. \quad (3)$$

Prior to an ablation procedure, equation (1) is modeled by fitting experimentally determined values of F, S, $F_{sat}$, and $S_{sat}$ (for different values of the power P and the time interval T) to an equation having a curve similar to that shown in FIG. 2. The values can be established using the lesion-producing apparatus described in PCT Patent Publication WO 2011/034925, which is herein incorporated by reference. For example, an equation of the form below may be assumed:

$$S_{sat} = A(1 - e^{-\frac{P}{cP}})(1 - e^{-\frac{f}{cF}})(1 - e^{-\frac{t}{cT}}), \quad (4)$$

where A and c are constants, and are generally pre-established. Alternatively, they may be determined during an actual ablation procedure, and Equation (4) may be used to find sets of values of F, P, and T needed to give a desired lesion size, as explained below. Ablation using the values may then be carried out.

Other equations may be substituted for Equation (4) to approximate the saturation effect, e.g., an equation describing an appropriately oriented hyperbola. In any case, the saturation effect that has been discovered indicates that the relation between the lesion size and force exerted by the catheter performing the ablation is not linear. Consequently, modeling a non-linear relationship between the two variables acts as a better predictor of lesion size than assuming a linear relationship.

During the ablation, contact force between the ablation electrode 32 and the wall 37 may be measured using a position sensor in conjunction with the positioning processor 22 (FIG. 1), or by any of the other techniques described above for verifying physical electrode contact with the target tissue.

In operation, two of the variables F, P, T are held constant, and the third is varied, either randomly or systematically, so as to produce a desired lesion size S by the ablation. In any case, the contact force is limited, so as not to exceed the saturation point ($F_{sat}$, $S_{sat}$).

In one embodiment, the power level and time interval are held constant, and the contact force is varied by the operator so as to generate the desired lesion size S when ablation power is applied for the specified time interval.

In another embodiment, the contact force is predetermined, and maintained by the operator during the catheterization. The power level is also predetermined. The time interval required to produce the desired lesion size S is then computed by solving equation (1) or equation (2).

In yet another embodiment, the time interval and the contact force are predetermined, the contact force being maintained by the operator as described above. The power required to produce the desired lesion size S is then computed by solving equation (1) or equation (2).

In all cases detection of a saturation point avoids the necessity of testing greater values of the variable parameter.

Figure 3:
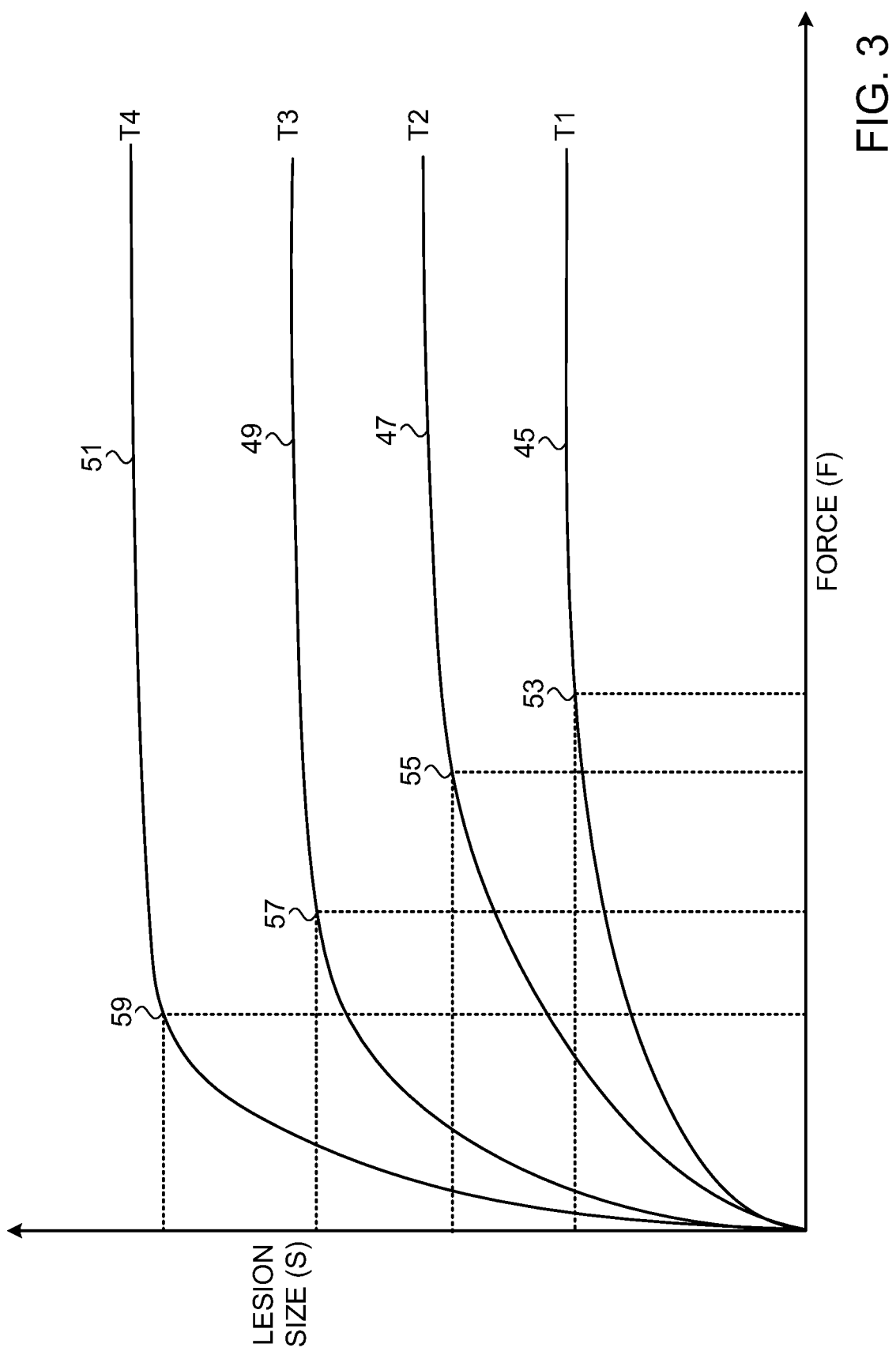
FIG. 3 shows an exemplary family of curves, showing lesion sizes in accordance with an embodiment of the invention.

The solutions to the equations in any of the above embodiments may be shown graphically, by reference to a family of curves developed prior to the ablation using the methods noted above. Reference is now made to FIG. 3, which shows an exemplary family of curves 45, 47, 49, 51, in accordance with an embodiment of the invention. Ablation is conducted at increasing time intervals T1-T4, respectively, with the ablation power level being constant, and the applied force (F) is variable. The curves correspond to saturation points 53, 55, 57, 59 ($F_{sat}$, $S_{sat}$) conveniently indicating a maximum force that can be applied by the operator, after which the lesion size fails to increase, and further indicating the time interval required to produce the lesion under the specified conditions. Similar families of curves may be constructed when the time interval is held constant and when the contact force is held constant. In any case respective regions of the curves lying to the left of the saturation points 53, 55 57 59 are referred to as unsaturated regions.

Figure 4:
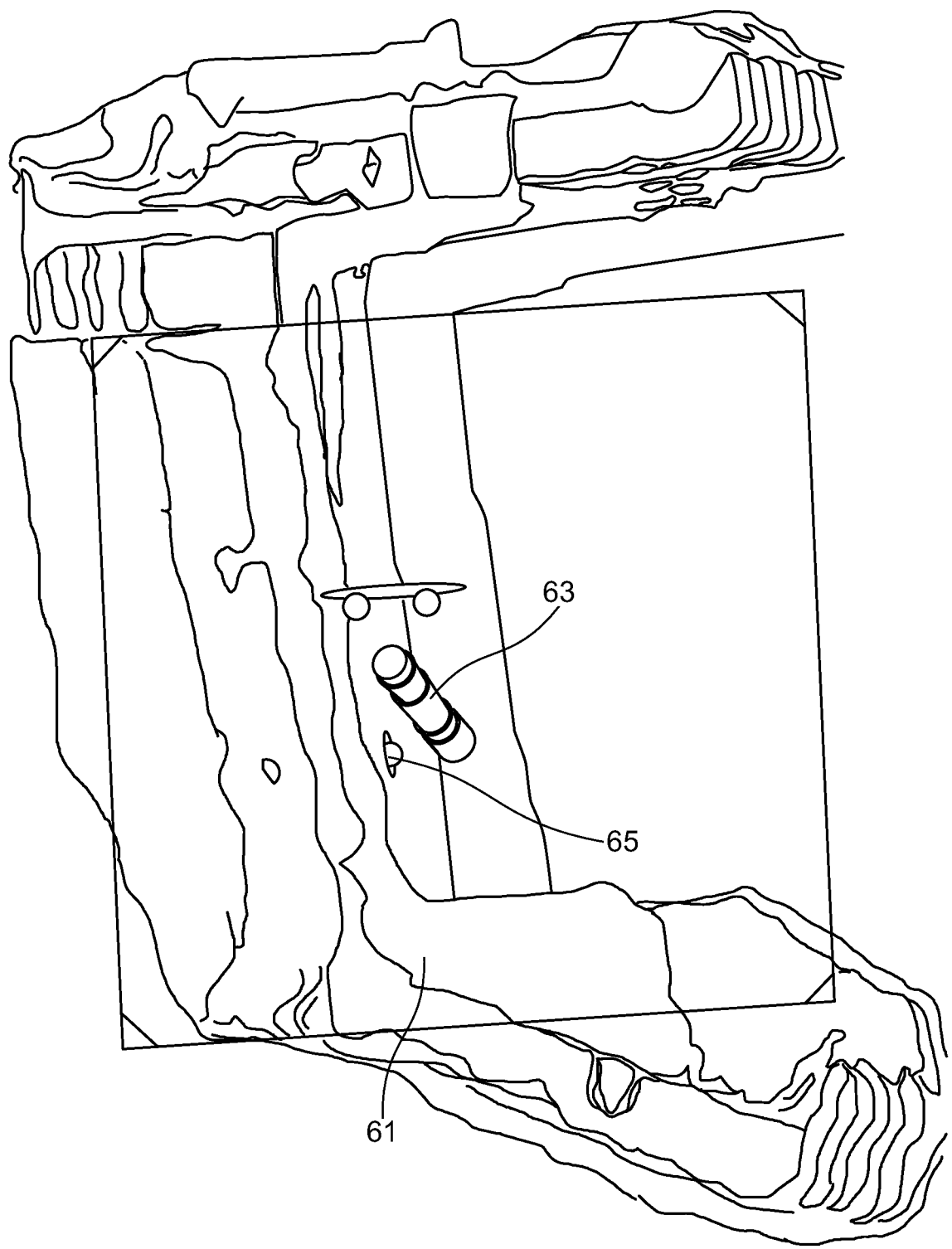
FIG. 4 is a screen display of a portion of a heart wall produced by a simulator of a cardiac ablation procedure, in accordance with an embodiment of the invention.

Reference is now made to FIG. 4, which is a screen display a portion of a heart wall 61 produced by a simulator of a cardiac ablation procedure, in accordance with an embodiment of the invention. A simulated catheter tip 63 is disposed near target tissue 65.

Figure 5:
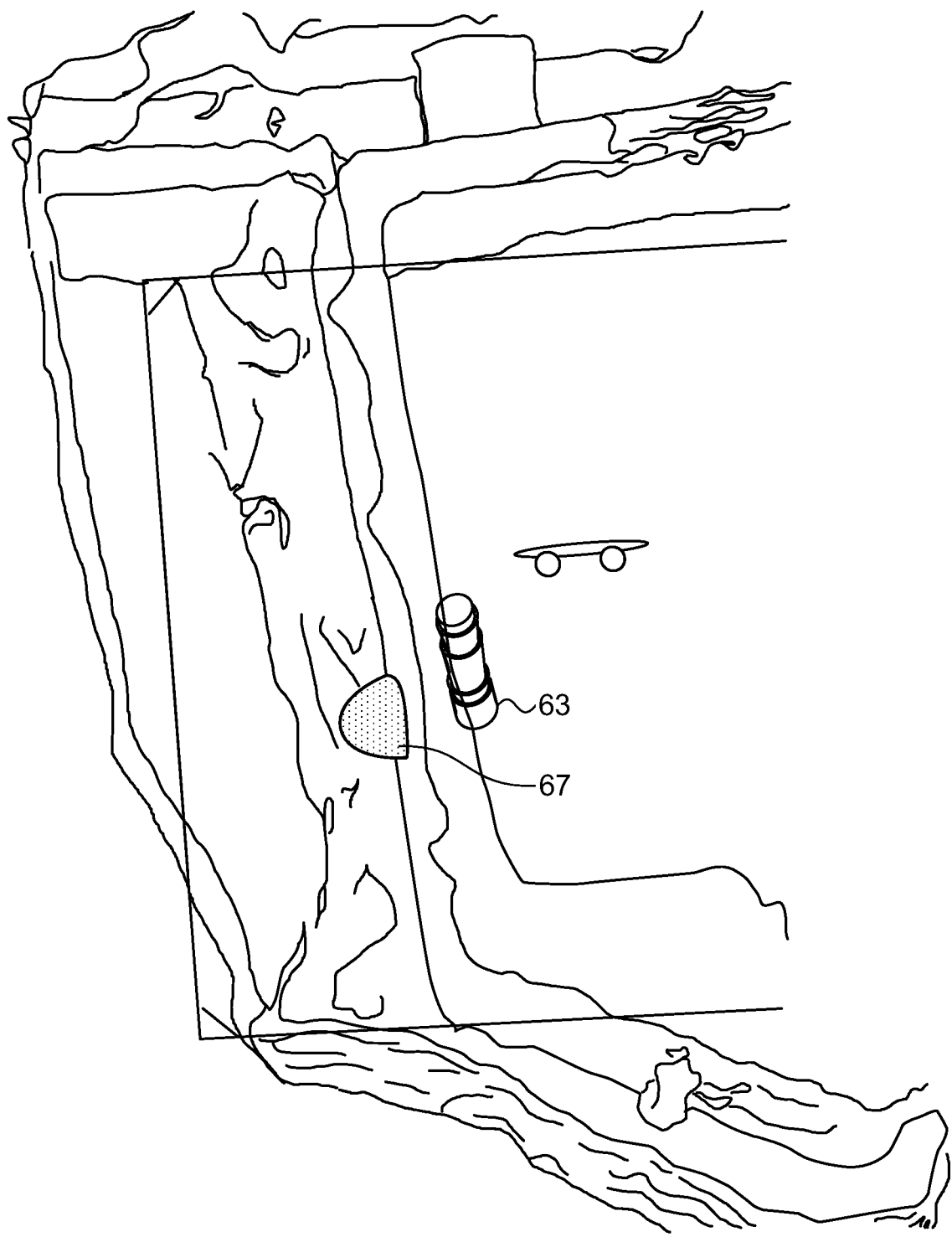
FIG. 5 is a screen display similar to FIG. 4, showing a predicted lesion produced according to an embodiment of the invention.

Reference is now made to FIG. 5, which is a screen display similar to FIG. 4, in accordance with an embodiment of the invention, except now a predicted lesion 67 is simulated, and displayed for the benefit of an operator. Equations (1) and (2) have been applied to determine a saturation point using the selected parameters. Typical values are:

P: 30 W;

F: 5-40 gmf, (where 1 gmf is equivalent to the weight of 1 gram of mass at standard gravity);

T: 60 sec.

Figure 6:
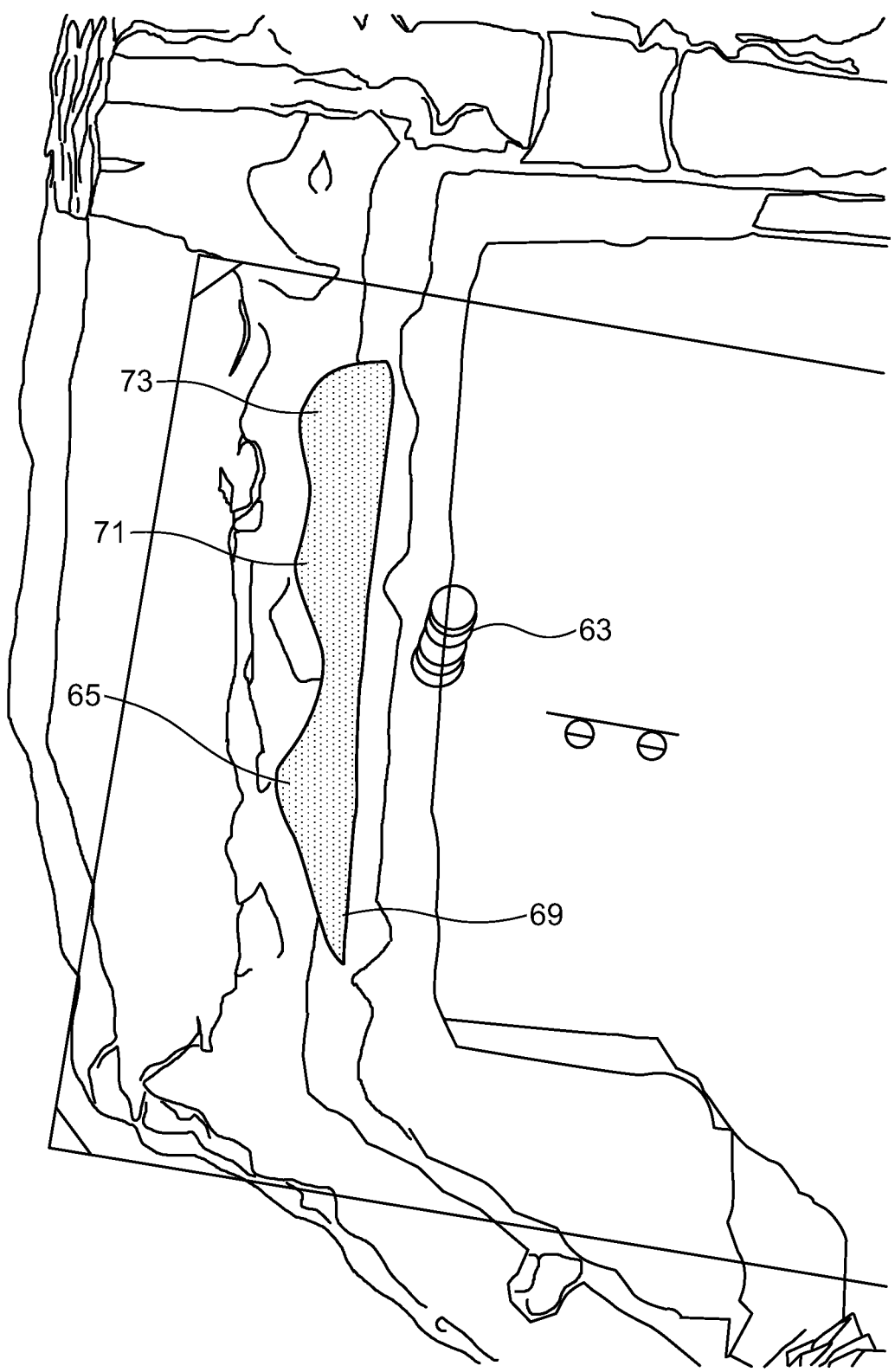
FIG. 6 is a screen display similar to FIG. 4, showing another predicted lesion produced according to an embodiment of the invention.

Reference is now made to FIG. 6, which is another screen display similar to FIG. 4 and FIG. 5, in accordance with an embodiment of the invention. The simulated ablation has progressed and a simulated confluent lesion 69 has formed as a result of ablations at the target tissue 65 and two other targets 71, 73.

Figure 7:
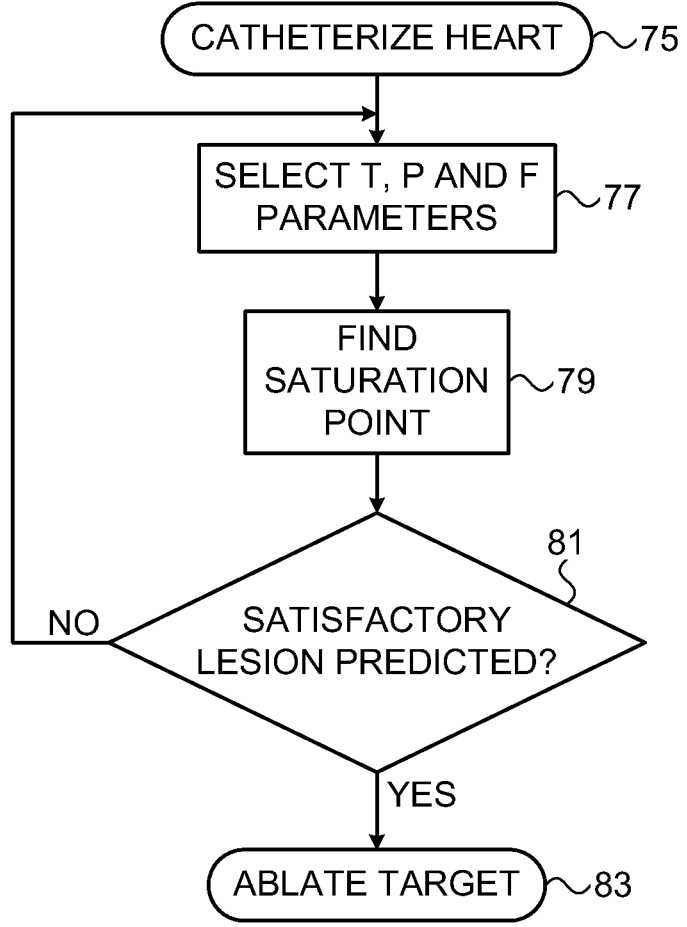
FIG. 7 is a flow chart of a method of ablation power control, in accordance with an embodiment of the invention.

Reference is now made to FIG. 7, which is a flow chart of a method of ablation power control, in accordance with an embodiment of the invention. At initial step 75 the subject heart is catheterized. It is assumed that an ablation target in the heart is concurrently determined using known methods, or has already been determined.

Next, at step 77, parameters are chosen as above. For example, for a given ablation time interval T and a given ablation power P, the lesion size S is predicted for a force F, applying equation (1). As noted above, it is also possible to hold the force F constant and vary either the time interval T or the ablation power P. The predicted lesions may be displayed for the operator, as shown in FIG. 4, FIG. 5 and FIG. 6.

Next, at step 79, the saturation point is determined using different values of the chosen parameters F, P, T, for example by applying equation (2). A variety of conditions may be examined concurrently, using known parallel processing techniques.

Control now proceeds to decision step 81, where it is determined if one of the predicted lesions sizes determined at step 77 under operating conditions and in an unsaturated region is suitable for ablation, If the determination at decision step 81 is negative, then control returns to step 77, and different parameters F, P, T are selected.

If the determination at decision step 81 is affirmative, then control proceeds to final step 83. The target may be ablated using the selected values of the parameters F, P, T.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for ablation, comprising the steps of:
   inserting a probe into a body of a living subject, the probe having an ablation electrode;
   prior to ablation and prior to the probe being put into a contacting relationship with a target tissue:
      selecting a contact force between the ablation electrode and the target tissue, a power level and a time interval;
      calculating a predicted lesion size that would result from placing the ablation electrode in the contacting relationship with the target tissue at the contact force while applying energy at the power level via the ablation electrode to the target tissue for ablation thereof for the time interval by modeling the lesion size as a non-linear function of the contact force, the power level and the time interval;
      iterating the step of calculating the predicted lesion size by increasing the contact force while keeping the power level and the time interval constant until a saturation point is determined, wherein the saturation point is determined to be when a further increase in the contact force fails to result in an increase of the predicted lesion size, wherein each calculated predicted lesion size has a corresponding known contact force, power level and time interval;
      establishing that one of the calculated predicted lesion sizes corresponding to an iteration is suitable for ablation;
   urging the ablation electrode into the contacting relationship with the target tissue; and
   ablating the target tissue using the corresponding known contact force, power level and time interval of the one of the calculated predicted lesion sizes established to be suitable for ablation.

2. The method according to claim 1, further comprising the step of graphically displaying the calculated predicted lesion size while iterating the step of calculating the predicted lesion size.

3. A method for ablation, comprising:
   inserting a probe into a body of a living subject, the probe having an ablation electrode;

prior to ablation and prior to the probe being put into a contacting relationship with a target tissue:

selecting a contact force between the ablation electrode and the target tissue, a power level, and a time interval;

calculating a predicted lesion size that would result from placing the ablation electrode in the contacting relationship with the target tissue at the contact force while applying energy at the power level via the ablation electrode to the target tissue for ablation thereof for the time interval by modeling the lesion size as a non-linear function of the contact force, the power level, and the time interval;

iterating the calculating the predicted lesion size by varying a selected one of the contact force, the power level and the time interval while keeping the remaining two of the contact force, the power level and the time interval constant until a saturation point is determined, wherein the saturation point is determined to be when a further increase in the selected one of the contact force, the power level and the time interval fails to result in an increase of the calculated predicted lesion size, wherein each calculated predicted lesion size has a corresponding known contact force, power level and time interval;

establishing that one of the calculated predicted lesion sizes corresponding to an iteration is suitable for ablation;

urging the ablation electrode into the contacting relationship with the target tissue; and ablating the target tissue using the corresponding known contact force, power level, and time interval of the one of the calculated predicted lesion sizes established to be suitable for ablation.

4. The method according to claim 3, further comprising graphically displaying the calculated predicted lesion size while iterating the calculating the predicted lesion size.

5. The method according to claim 3, wherein the iterating the calculating the predicted lesion size comprises varying the contact force and holding the power level and the time interval at constant levels until the saturation point is determined.

6. The method according to claim 3, wherein the iterating the calculating the predicted lesion size comprises varying the power level and holding the contact force and the time interval at constant levels until the saturation point is determined.

7. The method according to claim 3, wherein the iterating the calculating the predicted lesion size comprises varying the time interval and holding the contact force and the power level at constant levels until the saturation point is reached.

8. A method for ablation, comprising:

inserting a probe into a body of a living subject, the probe having an ablation electrode;

prior to ablation and prior to the probe being put into a contacting relationship with a target tissue:

selecting a contact force between the ablation electrode and the target tissue, a power level, and a time interval;

calculating a predicted lesion size that would result from placing the ablation electrode in the contacting relationship with the target tissue at the contact force while applying energy at the power level via the ablation electrode to the target tissue for ablation thereof for the time interval by modeling the lesion size as a non-linear function of the contact force, the power level, and the time interval;

iterating the calculating the predicted lesion size by varying a selected one of the contact force, the power level and the time interval while keeping the remaining two of the contact force, the power level and the time interval constant until a saturation point is determined, wherein the saturation point is determined to be when a further increase in the selected one of the contact force, the power level and the time interval fails to result in an increase of the calculated predicted lesion size, wherein each calculated predicted lesion size has a corresponding known contact force, power level and time interval;

establishing whether one of the calculated predicted lesion sizes corresponding to an iteration is suitable for ablation;

if none of the calculated predicted lesion sizes corresponding to an iteration is established to be suitable for ablation, then repeating the iterating the calculating the predicted lesion size by selecting a different value for at least one of the contact force, the power level, or the time interval, and repeating the establishing whether one of the calculated predicted lesion sizes corresponding to an iteration is suitable for ablation until one of the calculated predicted lesion sizes corresponding to an iteration is established to be suitable for ablation;

urging the ablation electrode into the contacting relationship with the target tissue; and ablating the target tissue using the corresponding known contact force, power level, and time interval of the one of the calculated predicted lesion sizes established to be suitable for ablation.

9. The method according to claim 1, further comprising graphically displaying the calculated predicted lesion size while iterating the calculating the predicted lesion size.

10. The method according to claim 8, wherein the iterating the calculating the predicted lesion size comprises varying the contact force and holding the power level and the time interval at constant levels until the saturation point is determined.

11. The method according to claim 8, wherein the iterating the calculating the predicted lesion size comprises varying the power level and holding the contact force and the time interval at constant levels until the saturation point is determined.

12. The method according to claim 8, wherein the iterating the calculating the predicted lesion size comprises varying the time interval and holding the contact force and the power level at constant levels until the saturation point is reached.

* * * * *